US005662929A

United States Patent [19]
Lagacé et al.

[11] Patent Number: 5,662,929
[45] Date of Patent: Sep. 2, 1997

[54] THERAPEUTIC LIPOSOMAL FORMULATION

[75] Inventors: Jacqueline Lagacé, St.-Laurent; Christian Beaulac, Yamachiche; Sébastien Clément-Major, St-Lambert, all of Canada

[73] Assignee: Universite de Montreal, Montreal, Canada

[21] Appl. No.: 363,416

[22] Filed: Dec. 23, 1994

[51] Int. Cl.$^6$ .......................... A61K 9/127; A61K 31/70
[52] U.S. Cl. .......................... 424/450; 514/36; 514/37; 514/38; 514/39; 514/40
[58] Field of Search .................... 514/36, 37, 38, 514/39, 40, 450

[56] References Cited

U.S. PATENT DOCUMENTS

| | | | |
|---|---|---|---|
| 4,235,871 | 11/1980 | Papahadjopoulos et al. | 424/450 |
| 4,753,788 | 6/1988 | Gamble | 424/1.21 |
| 4,952,405 | 8/1990 | Yau-Young | 424/423 |
| 4,981,692 | 1/1991 | Popescu et al. | 424/422 |
| 5,006,343 | 4/1991 | Benson et al. | 424/450 |

FOREIGN PATENT DOCUMENTS

WO93/23015  11/1993  WIPO.
WO94/12155  6/1994  WIPO.
WO94/12156  6/1994  WIPO.

OTHER PUBLICATIONS

Legacé et al., 1991, J. Microencapsulation 8:53–61.
Omri et al., 1994, Antimicrob. Agents Chemother. 38:1090–1095.
Merck Manual, 1992, 16th Edition, Merck Res. Lab.
Yoshimura et al., 1982, J. Bacteriol. 152:636–642.
Nicas et al., 1983, J. Bacteriol. 153:281–285.
Angus et al., 1982, Antimicrob. Agents Chemother. 21:299–309.
American Society for Microbiology, Manual of methods for general bacteriology. Washington, D.C. 1981, p. 185.
Lopez–Berestein et al., 1987, J. Clin. Oncology, 5:310–317.
Nacucchio et al., 1988, J. Microencapsulation 5:303–309.

*Primary Examiner*—Elli Peselev
*Attorney, Agent, or Firm*—Klauber & Jackson

[57] ABSTRACT

The invention relates to a liposomal formulation containing a therapeutic agent. The formulation of the invention when administered to animals, allows a substantial increase in antibacterial activity of the agent, through an enhanced penetration of the agent inside the bacterial cell. More specifically, the invention relates to a liposomal formulation containing at least one therapeutic agent such as an antibiotic and to a method of treatment of bacterial infections through the administration of such a formulation.

11 Claims, No Drawings

THERAPEUTIC LIPOSOMAL FORMULATION

BACKGROUND OF THE INVENTION

1. Field of the Invention

The invention relates to a liposomal formulation containing a therapeutic agent. Moreover, it relates to an original liposomal formulation allowing a modulated release of the therapeutic agent over time, as well as an increased penetration of a therapeutic agent such as an antibiotic into bacterial cells. The invention further relates to a method of treating bacterial infections in an animal through the administration of the formulation of the present invention.

2. Description of the Prior Art

Encapsulation of bioactive compounds in natural or synthetic matrixes has been extensively studied over the past decades. Advantages of such strategy of administration are numerous. First, it provides a protection from the inactivation or degradation of the bioactive compound. Secondly, it controls the kinetics of compound release, allowing the optimization of the blood concentration profile. This diminishes the deleterious effects of bioactive compounds with short half lives. In addition, it permits a reduction of the risk of toxicity.

Liposomes are closed microscopic vesicles that form spontaneously from phospholipids above their transition temperature, in the presence of excess water. Vesicles with a diameter ranging from 20 nanometers to several micrometers can be prepared. Multilamellar liposomes are made of concentric phospholipid bilayers separated by aqueous layers. Unilamellar liposomes consist of a single phospholipid layer surrounding an aqueous core. Liposomes can accommodate hydrophilic molecules in the aqueous spaces and lipophilic molecules in the lipid bilayers.

The potential of liposomes as vehicles for therapeutic agents, or therapeutic liposomal formulations, has been studied by several investigators. Successful treatments with liposomes against intracellular bacteria have been demonstrated (Lopez-Berestein et al., 1987, J. Clin. Oncology, 5:310–317; and Popescu et al., 1991, U.S. Pat. No. 4,981, 692). A number of studies have also shown that liposome-entrapped antibacterial agents increase the therapeutic indices of these agents as a result of decreased toxicity, modification of pharmacokinetics and tissue distribution parameters (Lagacé et al., 1991 J. Microencapsulation 8:53–61 and references therein; Omri et al., 1994, Antimicrob. Agents Chemother. 38:1090–1095).

The most widely used type of antibacterial agent is most certainly the antibiotics. Antibiotics can be subdivided in different groups which include the β-lactams, aminoglycosides, macrolides, lincomycin, clindamycin, tetracyclines, chloramphenicol, vancomycin, rifampin, quinolones, and sulfonamides.

Aminoglycosides are all potent bactericidal agents that share the same general range of antibacterial activity and pharmacokinetic behaviour. The members of the group are typified by the presence of aminosugars glycosidically linked to aminocyclitols. The main agents fall into two groups: the small group consisting of streptomycin, and its close relatives; and the large group which is subdivided into the neomycin group, the kanamycin group which is again subdivided into the kanamycins, tobramycin and their semi-synthetic derivatives amikacin and dibekacin and the important sub-group of gentamicins and their relatives, netilmicin and sissomicin.

The aminoglycosides inhibit protein synthesis in a variety of microorganisms and are used primarily to treat infections caused by organisms which are resistant to other antibiotics, particularly gram-negative bacteria such as but not limited to species of Escherichia, Enterobacter, Klebsiella, Pseudomonas, Salmonella. To different degrees the aminoglycosides are also active against *Staphilococcus aureus*, Staphilococcus epidermidis, Listeria and bacteria from the genera Mycobacteria.

Because aminoglycosides are highly polar cationic compounds, diffusion across the bacterial cell membrane is very limited and intracellular accumulation of the antibacterial agents is brought about by active transport. Many organisms display resistance to the older aminoglycosides. In addition, an increase in the resistance of microorganisms to the more recently introduced aminoglycosides is steadily rising. Increasing evidence suggests that acquired antibiotic resistance is often due to a balance between outer membrane penetration rate and the subsequent enzyme inactivation rate. Thus, the outer membrane barrier and the antibiotic-degrading enzymes are strongly synergistic. Moreover, while a newer aminoglycoside, by virtue of its insusceptibility to bacterial degrading enzymes, is active against strains resistant to older members of the group, can not be used to predict its activity in general, in view of the relative impermeability of a significant number of strains.

Although the aminoglycosides are useful for treating infections, their use can be accompanied by toxicity and side effects. The most important toxic effects are ototoxicity and nephrotoxicity. Because aminoglycosides can produce concentration-related oto-and nephrotoxicity, it is important to ensure that their plasma concentrations do not exceed toxic levels. It is equally important to ensure that fear of toxicity does not result in therapeutically inadequate dosage.

The encapsulation of aminoglycosides and β-lactam antibiotics into liposomal formulations by the dehydration-rehydration vesicle (DRV) method has been described (Lagacé et al., 1991, J. Microencapsulation 8:53–61). Disteroyl phosphatidyl-choline (DSPC) and dimyristoyl phosphatidyl-glycerol (DMPG), two synthetic phospholipids were used at a molar ratio 10:1 and at a lipid concentration of 16.5 umol/ml. The same liposomal formulation was tested "in situ" in an animal model of chronic pulmonary infection with *Pseudomonas aeruginosa* and permitted a marked increase of the residence time of antibiotic in lungs and a reduced systemic antibacterial agent absorption. Nevertheless, this liposomal aminoglycoside formulation did not show an improvement in the bactericidal activity as compared to free antibiotics and other controls (Omri et al., 1994, Antimicrob. Agents Chemother. 38:1090–1095). Other groups have disclosed aminoglycoside liposomal formulations (Da Cruz et al., 1993, WO 93/23015 and Proffitt et al., 1994, WO 94/12155). Nevertheless, the disclosed formulations fail to display a very drastic enhancement of the therapeutic activity of the antibiotic as compared to its activity in the free form. Indeed, the preferred aminoglycoside (netilmicin) liposomal formulation of Da Cruz et al., which comprises phosphatidylcholine (PC), cholesterol and phosphatidyl-inositol (PI), only shows a modest increase activity in vivo with the aminoglycoside as part of the liposomal formulation as compared to free aminoglycoside (at best by a factor of three). Proffitt et al., disclose a different aminoglycoside (amikacin) liposomal formulation comprising PC, cholesterol and distearoyl phosphatidylglycerol (DSPG). Although the Proffitt et al., formulation appears to be superior at enhancing the in vivo therapeutic activity of the aminoglycoside as compared to that of Da Cruz, this increase is still relatively low and dependent on the tissue (10-fold increase in spleen, 5-fold in liver and only 2-fold in lung). Importantly, the available liposomal formulations for use in treating bacterial infections do not appear to increase significantly the passage of the therapeutic agent through the bacterial membrane.

Cystic fibrosis (CF) is one of the most common lethal genetic diseases in humans. While the course of CF, varies greatly from patient to patient, it is largely determined by the degree of pulmonary involvement. In CF, deterioration appears unavoidable, and eventually leads to death. Although a CF patient prognosis has drastically improved in the second half of the century, the average survival is only 30 years of age. Of importance, a correlation between early colonization of Pseudomonas and a worse prognosis for CF patients has been observed. In addition, chronic lung infection due to *Pseudomonas aeruginosa* is the major cause of morbidity and mortality in patients wits cystic fibrosis (Omri et al., 1994, Antimicrob. Agents Chemother. 38:1090–1095; and Merck manual, 1992, 16th Edition, Merck Res. Lab.). In CF patients, *Staphylococcus aureus*, and *Haemophilus influenza* other Gram negative strains, are generally the early isolated pathogens. Such bacterial infections in CF patients are, in most cases, efficiently treated with antibiotics. A number of antibiotics are used for the antibacterial therapy, either alone or in combination. The choice of a particular antibiotic regimen depends on a number of factors which include the site and severity of the infection as well as the resistance/sensitivity profile of the microorganism. Of importance is the fact that high doses of antibiotics, especially aminoglycosides, as well as long-term antibiotic treatment are often indicated in CF patients.

*Pseudomonas aeruginosa* colonize more than 90% of CF adolescents. Efficient therapy targeted against *Pseudomonas aeruginosa* remains difficult and controversial (Omri et al., 1994, Antimicrob. Agents Chemother. 38:1090–1095). The usual standard therapy for CF patients colonized with this microorganism involves the use of an aminoglycoside or β-lactam alone or in combination. These antibacterial agents require frequent high-dose parenteral administration in order to achieve therapeutically effective concentrations in serum, particularly against biofilm cells formed by the mucoid phenotype of *P. aeruginosa*. It should be noted that the outer-membrane (OM) permeability of *P. aeruginosa* is only about 1–8% that of *E. coli*, as assessed by antibiotic penetration rates (Yoshimura et al., 1982, J. Bacteriol. 152:636–642; Nicas et al., 1983, J. Bacteriol. 153:281–285; and Angus et al., 1982, Antimicrob. Agents Chemother. 21:299–309). It has also been reported that prolonged or repeated treatment with antibiotics has been associated with gradually decreasing susceptibility of this organism and with accelerated clearance of antibiotics in these patients (Omri et al., 1994, Antimicrob. Agents Chemother. 38:1090–1095; and references therein). Thus, although the use of liposomes as a vehicle for antibiotics, has been shown in "in vitro" experiments to be a promising avenue for the treatment of *P. aeruginosa* (Lagacé et al., 1991, J. Microencapsulation 8:53–61; and Nacucchio et al., 1988, J. Microencapsulation 5:303–309), the design of a liposomal formulation permitting a significant improvement in the activity of the antibiotic as well as a significantly improved penetration inside the bacterial cell is yet to emerge. The design of such a liposomal formulation would be of tremendous importance in the treatment, and/or prophylaxis of bacterial infections in CF patients, and perhaps on the prognosis of these patients.

Although microorganism resistance to antibiotics has long been recognized, it continues to be an important health problem world-wide. Furthermore, based on the relative impermeability of numerous strains to antibiotics, the design of newer more efficient versions thereof, which can overcome the strain-based enzymatic degradation, still does not solve the significant hurdle of getting the antibiotic through the impermeable membrane or through an exopolysaccharide layer of the bacteria and to its site of action. Furthermore, the problem of increased resistance to antibiotics is compounded by the misuse of these agents (Merck manual, 1992, 16th Edition, Merck Res. Lab.). For example, because of the antibiotic resistance of microorganisms, which is more acute with older types of antibiotics, practitioners are often prompted to use a newer generation antibiotic, thereby contributing to the increased resistance of microorganisms to newer generation antibiotics. The large scale use of antibiotics in animals, including but not limited to dairy cows, and the presence of these antibiotics in milk or in the environment, is yet another contributor to the increase in microorganism resistance to antibiotics.

It would be of tremendous importance for the clinician to be able to increase the activity of antibiotics thereby potentially permitting a lowering of the doses required to attain the aimed anti-bacterial action. Furthermore, such increase in antibiotic activity would permit a more efficient use of older generation antibiotics, thereby moderating the increase in microorganism resistance to new generation antibiotics.

It would be a very significant advantage for the clinician, veterinarian or the like, to be able to use a liposome formulation containing an anti-bacterial agent, such as an antibiotic, wherein the liposomal formulation significantly improves the anti-bacterial activity of the agent, not only because of increased circulation time, and lower toxicity, but also because this formulation comprises phospholipids that markedly improve the penetration of the agent in a bacterial cell. It would further be of great advantage if the formulation also permitted a marked increase in the penetration of the anti-bacterial agent through the outer membrane (OM) and mucoid exopolysaccharides such as those secreted by mucoid variants of bacteria such as that of *Pseudomonas aeruginosa*.

In addition, it would be a tremendous advantage to have access to a therapeutic liposomal formulation, wherein the composition of the formulation permits modulated release of the therapeutic agent, over time thereby reducing side-effects and prolonging the action of the agent.

SUMMARY OF THE INVENTION

Based on physico-chemical properties of phospholipids, many new liposomal formulations were designed in order to promote the "in vivo" bactericidal efficacy of liposomal aminoglycosides while maintaining encapsulation efficiency, prolonged antibiotic residence time in targeted organ and low toxicity. Those new liposomal formulations were submitted to different "in vitro" and "in vivo" tests.

The present invention relates to the successful design of liposomal formulations which contain in one embodiment an aminoglycoside, display a very effective "in vivo" bactericidal activity compared to free antibiotics and fulfill the other following needs: modulated release of the therapeutic agent over time, maintenance of therapeutic agent encapsulation efficiency, prolonged antibiotic residence time in targeted organ and low toxicity.

The present invention further relates to liposomes containing a therapeutic agent, and characterized by an original formulation allowing increased penetration of the therapeutic agent into bacterial cells and through bacterial mucoid exopolysaccharides. An example of therapeutic agent is an antibiotic, but is not limited thereto. Through its increased penetration of bacterial cells, the liposomal formulation of the present invention showed a marked improvement of the "in vivo" bactericidal efficacy while free antibiotic showed no or little bactericidal activity.

In addition, the present invention relates to the pharmaceutical or veterinary use of the liposomal formulations of the present invention in the treatment or prophylaxy of bacterial infections.

It is an object of the present invention to provide a low rigidity liposomal formulation comprising a therapeutic agent, wherein the interaction between the components of the formulation permit a slow but constant release of the therapeutic agent over time as well as an enhanced penetration of the agent inside a bacterial cell.

It is an other object of the invention to provide a liposomal formulation for the treatment of bacterial infections, wherein the liposomal formulation comprises a combination of lipids together with a therapeutic agent.

The liposomal formulations of the present invention have not been specifically described in the prior art. Although such formulations, appear to fall broadly within the claims of WO 93/23015, WO 94/12155, U.S. Pat. No. 4,235,871 and U.S. Pat. No. 4,981,692, they are not specifically identified therein and there is no suggestion of any special activity inherent in them.

In addition, before achieving the proper formulations of the invention, a great number of formulations also generally described in WO 93/23015, WO 94/12155, U.S. Pat. No. 4,235,871 and U.S. Pat. No. 4,981,692 were prepared. These include DSPC:DMPG, DSPC:DPPC, DPPC:DMPC, in a molar ratio of 15:1 and 10:1, with or without cholesterol (at a molar ratio of 1, ie: 10:1:1). None of these formulations, also comprising tobramycin, showed a marked improvement of antibacterial activity when compared to free tobramycin. Furthermore, these experiments would suggest that the presence of cholesterol in the therapeutic liposomal formulation improves liposomal stability in a way that goes against the desired therapeutic activity of the formulation.

Thus, it is an object of the invention to provide a liposomal formulation which is free of stabilizing agents that would affect the desired therapeutic activity of the formulation and the desired kinetics of therapeutic agent release from the liposomes.

In accordance with one aspect of the present invention, there is provided a low rigidity multilamellar liposomal formulation, free of cholesterol, comprising a neutral lipid, an anionic lipid and at least one therapeutic agent, wherein the liposomal formulation enhances the penetration of the therapeutic agent inside a bacterial cell.

In accordance with another aspect of the present invention, there is provided a method of treating a bacterial infection in an animal, comprising an administration of a pharmaceutically or veterinarilly suitable dose of the liposomal formulation.

In accordance with an additional aspect of the present invention, there is provided a liposomal formulation which permits the penetration of the entrapped therapeutic agent through the exopoiysaccharide layer of a bacteria. Hence, the liposomal formulation of the present invention provides an increased efficacity in the treatment of mucoid bacteria.

In accordance with yet another aspect of the present invention, there is provided a use of the liposomal formulation for the treatment, prophylaxy or diagnosis of a bacterial infection in an animal, comprising an administration of a pharmaceutically or veterinarilly suitable form of the formulation.

Since a multitude of therapeutic agents can be entrapped within the liposomes of the invention, in the specification and appended claims, it is to be understood that the term therapeutic agent is designed to include, but is not limited to antibiotics, bioactive molecules, such as proteins or parts thereof, nucleic acids or part thereof, amino acid analogs or nucleoside analogs, as well as other medically or veterinarilly useful agents such as contrast materials (e.g. dyes) and diagnostic materials as well as growth factors, hormones such as corticosteroids or the like. Furthermore, it is to be understood that the term therapeutic agent should be taken in a broad sense so as to also include a combination of at least two therapeutic agents.

In the specification and appended claims, the term lipid is designed to include, but is not limited to saturated or non-saturated lipids, or synthetic or derived from natural sources, provided that the lipid-therapeutic agent composition displays fluidity/stability which is compatible with the penetration of the therapeutic agent inside a bacterial cell and/or its modulated release.

Similarly, the term bacterial infections should be construed to include, but not limited to Gram negative bacteria such as genera Salmonella, or Pseudomonas, to Gram positive bacteria such as the genera Mycobacteria.

Other features and advantages of the invention will be apparent from the description of the preferred embodiments given hereinafter. However, it should be understood that the detailed description, while indicating preferred embodiments of the invention, are given by way of illustration only, since various changes and modifications within the spirit and scope of the invention will become apparent to those skilled in the art.

DETAILED DESCRIPTION OF THE INVENTION

This invention provides a therapeutic liposomal formulation allowing an increased penetration of therapeutic agent into bacterial cells and through bacterial mucoid exopolysaccharides. The liposomal formulation is prepared by lyophilisation, rehydration and extrusion under pressure. Liposomes have in a preferred embodiment, an average size of 0.6 um to 0.2 um and are comprised of a neutral lipid and a negatively charged lipid. The molar amount of negatively charged lipid is 6.5% to 11% of total lipid and the encapsulation efficiency is typically greater than 20%. When administered "in situ" to animals, the liposomal therapeutic agent formulation not only prolongs the therapeutic agent residence time and reduces its toxicity, but also increases its therapeutic activity. An embodiment of such formulation contains an antibiotic as therapeutic agent. In another embodiment, the liposomal formulation serves for the treatment of bacterial infections, and comprises a combination of phosphatidylcholine, a neutral phospholipid, and phosphatidylglycerol, an anionic phospholipid, at a ratio of 10:1 to 15:1, together with an therapeutic agent.

In an other preferred embodiment, the formulation contains an aminoglycoside as antibiotic. One example of aminoglycoside is tobramycin. Such a liposomal aminoglycoside formulation shows: 1) high bactericidal activity against microorganisms which are resistant during antibiotherapy in mammals; 2) high therapeutic agent encapsulation efficiency; 3) prolonged antibiotic residence time in targeted organ; 4) low toxicity; and 5) a modulated, gradual release of the encapsulated therapeutic agent over time.

The present invention also provides a therapeutic liposomal formulation which permits a modulated release of the therapeutic agent over time and hence permits a well-controlled release of the therapeutic agent. The present invention also provides a liposomal formulation that could serve as a diagnostic tool. Numerous types of bioactive agents could be coupled to the liposomes of the invention, for example antibodies, in order to target a specific tissue or cell type. The detection of the target can be assessed according to known methods, including for example the use of a label, radioactive or not, or a dye entrapped in the liposomes. One of numerous examples of the diagnostic use of the liposomal formulations of the invention is to target a tumoral antigen, through an antibody specific to this antigen, in order to detect, quantify or analyze the presence of metastases.

The therapeutic agent selected will depend upon the organism causing the infection. Suitable antibiotics include but are not limited to: penicillin, ampicillin, netacillin, carbencillin, tetracycline, tetracycline hydrochloride, oxtetracycline hydrochloride, chlortetracycline hydrochloride, 7-chloro-6-dimethyltetracycline, doxycycline, doxycycline monohydrate, methacycline hydrochloride, minocycline hydrochloride, rolitetracycline, dihydrostreptomycin, streptomycin, gentamicin, kanamycin, neomycin, erythromycin, carbomycin, oleandomycin, troleandomycin, Polymysin B, collistin, cephalothin sodium, cephaloridine, cephaloglycin dehydrate, and cephalexin monohydrate.

If the site of infection or affliction is external or accessible the liposome-entrapped therapeutic agent can be applied topically.

Bacterial agents contemplated herein include but are not limited to: Moraxella spp., Costridium spp., Corynebacterium spp., Diplococcus spp., Flavobacterium spp., Hemophilus spp., Klebsiella spp., Leptospira spp., Mycobacterium spp., Neisseria spp., Propionibacterium spp., Proteus spp., Pseudomonas spp., Serratia spp., Escherichia spp., Staphylococcus spp., Streptococcus spp., and bacteria-like organisms including Mycoplasma spp. and Rickettsia spp.

Aminoglycoside will be understood to mean aminoglycosides and analogues and derivatives thereof, including streptomycin, dehydrostreptomycin, tobramycin, neomycin B, paromycin, ribostramycin, lividomycin, kanamycin A and B, viomycin, gentamicin (including $C_1$, $C_{1a}$ and $C_2$), sisomicin, netilimicin and amikacin.

β-lactams will be understood to refer to synthetic, semi-synthetic and natural penicillins, cephalosporins, monobactams, and thinamycins, such as oxacillin, cephapirin, aztreonam and imipenem.

Depending upon the purpose of delivery, the liposomal formulation may be administered by a number of routes: in man and animals these include but are not limited to injection (e.g., intravenous, intraperitoneal, intramuscular, subcutaneous, intraauricular, intramammary, intraurethrally, etc.), topical application (e.g., on afflicted areas), and by absorption through epithelial or mucocutaneous linings (e.g., ocular epithelia, oral mucosa, rectal and vaginal epithelial linings, the respiratory tract linings, nasopharyngeal mucosa, intestinal mucosa, etc.).

The mode of administration of the preparation may determine the sites and cells in the organism to which the compound will be delivered. Liposomes can be administered alone but will generally be administered in admixture with a pharmaceutical carrier selected with regard to the intended route of administration and standard pharmaceutical practice. The preparations may be injected parenterally, for example, intraperitoneally, intraarterially or intravenously. The preparations may also be administered via oral, subcutaneous, intramuscular and, of course, intramammary routes. For parenteral administration, they can be used, for example, in the form of a sterile aqueous solution which may contain other solutes, for example, enough salts or glucose to make the solution isotonic. Other uses, depending upon the particular properties of the preparation, may be envisioned by those skilled in the art. Delivery of the liposomal formulation by way of an aerosol is also contemplated as a preferred method of administration. For example, but not limited thereto, the formulations of the present invention could be used in the treatment of respiratory diseases. Asthma is one of the numerous diseases for which these formulations could be used.

For administration to animals including humans in the curative treatment of disease states, the prescribing medical professional will ultimately determine the appropriate dosage for a given subject, and this can be expected to vary according to the agent, weight, and response of the animal as well as the nature and severity of the disease. The dosage of therapeutic agent in liposomal form can according to the present invention be lower than that employed for the free therapeutic agent. In some cases, however, it may be necessary to administer equal or higher doses. It is also contemplated that periodic treatments or different cycles of treatment might be beneficial.

The route of delivery of liposomes can also affect their distribution in the body. Passive delivery of liposomes involves the use of various routes of administration, e.g., intravenous, subcutaneous and topical. Each route produces differences in localization of the liposomes. Two common methods used to actively direct the liposomes to selected target areas are binding either antibodies or specific receptor ligands to the surface of the liposomes. Antibodies are known to have a high specificity for their corresponding antigen and have been shown to be capable of being bound to the surface of liposomes, thus increasing the target specificity of the liposome encapsulated drug.

The present invention further provides liposomal aminoglycoside or β-lactam formulations preferably containing tobramycin and the following synthetic lipids: dipalmitoylphosphatidylcholine (DPPC) and dimirystoylphosphatidylglycerol (DMPG). Other suitable phosphatidylcholines and phosphatidylglycerols include those obtained from soy, egg or plant sources or those that partially synthetic.

Depending upon the desired application, the purpose of delivery, the route of delivery, the target, and other parameters relating to the use of the formulation, the size of the liposomes can be adapted according to well known methods. For example, it is well known that large liposomes are better suited for a topical application while smaller liposomes are preferred for intravenous administration. Further, the size of the liposomes affect their capacity of being phagocytized by macrophages. Thus, the size of the liposomes can be adapted in order to favor a route of administration, to favor retention in the reticulo endothelial organs or to favor phagocytosis (to treat bacteria inside the macrophage for example). The sizes of the liposomes contemplated range from the nanometer to the micron, preferably between 100 nm to 1 um. In a preferred embodiment the size of the liposomes range between approximately 200 nm to 600 nm. Such a liposomal formulation is compatible with an aerosol administration of the formulation for delivery to the lungs of an animal.

A preferred formulation includes liposomes comprising an encapsulated aminoglycoside wherein the liposomes are multilamellar vesicles having an average size ranging between 0.2 um and 0.6 um. A preferred ratio of DPPC:DMPG is about 5:1 to 20:1 and a preferred therapeutic agent to total lipid ratio is from about 1:1 to 1:10. Other preferred formulations include suitable lipids like phosphatidylcholines and or phosphatidylglycerols present individually or in mixture, in a molar ratio ranging from about 0.01 to 20. Other preferred formulations include formulations where the therapeutic agent to total lipid ratio is from 1:10 to 1:1.

According to the present invention, the method of preparation of the multilamellar liposomes could be divided in 5 major steps. Lipids are dissolved in chloroform (about 1 mg lipid/ml chloroform or more) and the solution is evaporated to form a lipid film between room temperature and 60° C. The lipid mix is preferably negatively charged and the resulting lipid concentration ranges from about 5 mM up to 130 mM. The liposomal preparations are typically mixtures of two components or more: a phosphatidylcholine and a negatively charged molecule such as a phosphatidylglycerol with each component of the liposomal preparation in molar ratios of 40–90% and 5–60%, respectively. A preferred combination is dipalmitoylphosphatidylcholine (DPPC): dimirystoylphosphatidylglycerol (DMPG) at a ratio of 10:1 to 15:1, with total lipid concentration ranging from 5 to 85 mM. The resultant negatively charge lipid induces high antibiotic encapsulation efficiencies while the lipidic formulation promotes increased penetration of antibiotics in bacterial cells. The lipidic film is hydrated with an aqueous solution of antibiotic or with phosphate buffered saline (PBS) diluted 1:20. The concentration of antibiotic can vary from 0.01 mg/ml to 150 mg/ml. The preferred concentration is 10 mg/ml up to 40 mg/ml. The antibiotic is preferably an aminoglycoside as cited herein or a β-lactam but other antibiotics and non-antibiotic therapeutic agents may also benefit from the processes of the present invention.

Following hydration of the lipid film and formation of multilamellar liposomes, the preparation is subjected to freezing either in liquid nitrogen (−170° C.) or for two hour in a deep freezer (−70° C.) followed by lyophilization in a freeze dryer at 5 mtorr for 24 h. Lyophilized samples are conserved at −70° C. or −20° C. until use. For utilization, powder is rehydrated with an antibiotic solution (10 mg/ml to 40 mg/ml) at ⅛ portion of the initial volume with vigorous vortexing followed by incubation at 65° C. for 60 min. vortexing each 10 min. The suspension is then brought up to the 50% initial volume with buffered saline solution and vigorously vortexed again. Preferably, multilamellar vesicles are extruded through successively smaller-pore polycarbonate membranes from 1 um down to 0.2 um or as desired to achieve a gradual reduction in liposome size. Finally the sized mixture is centrifuged 2 times, for 20 min. at 5,000 g and the pellet resuspended in saline solution. The determination of tobramycin in liposomes was performed by high-performance liquid chromatography (HPLC).

A particularly important embodiment of the invention produces liposome/aminoglycoside formulation allowing a marked increased penetration of antibiotic into bacterial cells. In this embodiment the lipid mixture is dipalmitoylphosphatidylcholine (DPPC): dimirystoylphosphatidylglycerol (DMPG) at a ratio of 1:10 and 1:15, with total lipid concentration ranging from 5 to 85 mM. The final liposomal/aminoglycoside formulation had a diameter of about 0.4 uM and possessed an encapsulation efficiency of 20% and a therapeutic agent lipid ratio of 1:1. The improved bactericidal efficacy that results is related to the fact that the therapeutic agent is not only incorporated into liposomes but is incorporated in an original combination of phospholipids that markedly improves the penetration of therapeutic agent in bacterial cells and through mucoid exopolysaccharides secreted by *Pseudomonas aeruginosa*.

The liposomal/antibiotic formulations of the invention may be targeted with monoclonal antibodies or other molecules to a particular tissue or cell, such as a bacterial cell.

The present process for aminoglycoside encapsulation is a very significant improvement over earlier protocols using encapsulated aminoglycoside since low concentration of encapsulated aminoglycoside kills bacteria while with free antibiotic, $10^7$ c.f.u. are enumerated (see below).

EXAMPLE 1

Tobramycin liposomal formulation

The following examples describe analysis of liposome aminoglycoside formulations prepared as described above, wherein the aminoglycoside was tobramycin, the lipid mixture was dipalmitoylphosphatidylcholine (DPPC) :dimirystoylphosphatidyiglycerol (DMPG) at a ratio of 10:1 or 15:1, with total lipid concentration ranging from 5 to 85 mM. Hydration took place with phosphate buffered saline diluted 1:20, followed by freezing at −70° C. and lyophilization. Rehydration was made by adding antibiotic solution (10 mg/ml) at ⅛ portion of the initial volume, followed by filling to 50% of the initial volume with phosphate buffered saline. Liposomes were extruded first through a 1 um filter, followed by extrusion through 0.6 and 0.4 um polycarbonate membranes and centrifugation two times at 5,000× g for 20 min. and resuspended in PBS.

EXAMPLE 2

Physical and biological characteristics of different tobramycin-liposomal formulations Different liposomal formulations were prepared according to Example 1 and analyzed by differential scan colorimetry. Using differential scan calorimetry, the temperatures of phase transition ($T_c$) were calculated for the tobramycin-liposomal formulations listed in Table 1. All these formulations were then tested in vitro to assess the antibiotic kinetics of liberation from the liposomes. In addition, these formulations were tested in a non-infected mouse model as previously described (Omri et al. 1994, Antimicrob. Agents Chemother. 38:1090–1095) to assess the persistence of the liposomes in the lung. Only the DPPC/DMPG 10:1, 15:1 and DSPC. (Disteroylphosphatidylcholine)/DMPC (dimirystoylphosphatidylcholine) 15:1 liposomal formulations (shown in Table 1) exhibited the following characteristics: liberation of gradual and convenient amounts of antibiotic by virtue of their fluidity/stability characteristics. These liposomal formulations were further tested in animal model of chronic pulmonary infection to examine their antibacterial efficacy. Contrary to the two DPPC/DMPG formulations, the DSPC/DMPC formulation was shown to be inactive in this animal model. In addition, some formulations displaying a temperature of phase transition comparable to that of the two DPPC/DMPG formulations although showing the desired fluidity/stability characteristics were shown to be inefficient in the uninfected animal model. Of note, the addition of cholesterol to the formulation described in Table 1 brought the $T_c$ to a minimum value of 60° C. Such formulations were incompatible with modulation of gradual antibiotic liberation and suitable interactions with bacteria. Thus, in order to maintain the desired characteristic of the liposome formulation, a low rigidity of the liposomes seems required. This low rigidity can be achieved by maintaining a low temperature of phase transition (below the body temperature of the animal to which the formulation is to be administered) and avoiding the use of cholesterol in the formulation.

TABLE 1

Temperature of phase transition ($T_c$ of different tobramycin liposomal formulation

| Phospholipids | ratio | $T_c$ |
|---|---|---|
| DSPC/DMPG | 15:1 | 44 |
| DSPC/DMPC | 15:1 | 42 |
| DSPC/DPPC | 15:1 | 46 |
| DSPC/DMPG | 10:1 | 40 |
| DSPC/DMPC | 10:1 | 42 |
| DSPC/DPPG | 10:1 | 45 |
| DPPC/DMPG | 10:1 | 29.5 |
| DPPC/DMPG | 15:1 | 35 |

EXAMPLE 3

Pulmonary retention of the therapeutic agent

As briefly alluded to in Example 2, studies of pulmonary retention were done with liposomes prepared with a 10:1 molar ratio of DPPC:DMPG, as prepared in Example 1, in BALB/c mice (Charles River), and using free tobramycin as control. The animals were injected intracheally as previously described (Omri et al., 1994, Antimicrob. Agents Chemother. 38:1090–1095) with one dose of 50 ul (200 ug) of the free and liposomal tobramycin preparations and lungs, kidneys and blood were collected at fixed times (Table 2). Lungs and kidneys were removed aseptically, weighed, and then homogenized in cold sterile PBS (40% [wt/vol]) for 30 s with a Polytron homogenizer. Tobramycin levels in both homogenized tissues and sera were measured by HPLC. Groups of three mice were used for each time value.

TABLE 2

Comparative antibiotic concentrations following adminstration of free and liposome-encapsulated tobramycin in mice

| | Cong (ug/pair of lungs) | | Conc (ug/pair of kidneys) | | Sera ug/ml | |
|---|---|---|---|---|---|---|
| Time (h) | Free tobra | Lipo-somes | Free tobra | Lip | Free tobra | Lip |
| 0.25 | 43 | 58 | ND* | ND | ND | ND |
| 1 | 11 | 27 | 25 | 19 | UD† | 5 |
| 8 | UD | 46 | ND | ND | ND | ND |
| 24 | UD | 73 | ND | ND | ND | ND |
| 32 | UD | 17 | ND | ND | ND | ND |
| 48 | UD | 15 | UD | 13 | UD | UD |

*ND: not done;
†UD: undetectable

Administration of liposomal aminoglycoside formulation prepared according to this invention, resulted in a prolonged pulmonary retention time of the encapsulated form of tobramycin in lungs compared with that of the free therapeutic agent. It is to be noted, however, that the concentration of tobramycin decreases with time with the DPPC:DMPG formulation shown in Table 2. This result is in contrast to that of a DSPC:DMPG (10:1) formulation which showed a constant concentration of tobramycin over time, and hence a high stability of the liposomes (Omri et al., 1994, Antimicrob. Agents Chemother. 38:1090–1095, also see below).

EXAMPLE 4

Bactericidal activity

To evaluate the bactericidal efficacy of a liposomal aminoglycoside formulation produced according to the present invention, male, pathogen-free, Sprague-Dawley rats weighing 175 to 225 g (Charles River) were used. Chronic infection in lungs was established by intratracheal administration of $5 \times 10^5$ CFU of *Pseudomonas aeruginosa* PA 508 (mucoid phenotype) prepared in agar beads. It is to be pointed out that this rat model for chronic pulmonary infection is widely recognized as the most appropriate animal model for chronic pulmonary infections in human CF patients. After 3 days, three doses (600 ug) of free or liposome-encapsulated tobramycin were given intratracheally at intervals of 16 h. The lipid mixture were DPPC:D-MPG at a molar ratio of 10:1 (formula no 1) and DPPC:D-MPC at a molar ratio of 15:1 (formula no 2). Sixteen hours after the last treatment, the animals were sacrificed and the entire lungs were removed aseptically, weighed and homogenized as described previously for mice. Serial 10-fold dilutions of the homogenates in cold PBS were made and spread in triplicate on proteose peptone agar plates. Identification of *P. aeruginosa* was confirmed by specific cultures. CFU were counted after 24-h incubations at 37° C. under 5% $CO_2$. Counts were expressed in log CFU per pair of lungs. PBS and PBS-liposomes were used as controls. The results are listed in Table 3.

TABLE 3

Bactericidal effect of liposomal tobramycin on *P. aeruginosa* in infected rat lung tissues

| Regimen | # rats | cfu/pair of lungs | log cfu/pair of lungs |
|---|---|---|---|
| PBS only | 2 | $1.40 \times 10^6$ | 6.15 |
| liposome-PBS (formula no. 1) without tobramycin | 2 | $2.32 \times 10^7$ | 7.36 |
| liposome-tobra (formula no 1‡) | 5 | <significant count* | <significant count |
| liposome-PBS (formula no 2)† | 3 | $2.11 \times 10^7$ | 7.32 |
| liposomal tobra (formula no. 2)* | 6 | $1.83 \times 10^6$ | 6.26 |
| free tobramycin | 5 | $1.25 \times 10^7$ | 7.10 |

‡formula no 1: formula according to the present invention used here at a molar ratio 10:1, DPPC:DMPG.
*None or only rare cfu (0 to 4) were visible on plates spreaded in triplicate with undiluted lung samples. In accordance with the American Society for Microbiology, Manual of methods for general bacteriology. Washington, D.C., 1981, p. 185, cfu counts < 30 are not statistically significant.
†The formula no 2 was prepared with synthetic DSPC:DMPC at a molar ratio of 15:1. This formulation like a formulation previously described (Omri et al., 1994, Antimicrob. Agents Chemother. 38:1090–1095) at 10:1 molar ratio of DSPC:DMPG represents other liposomal formulations without improved bactericidal efficacy when compared to the activity of free antibiotic against *P. aeruginosa*.

A second experiment to study the bactericidal effect of the liposomal tobramycin preparation produced according to the present invention was carried out as for Table 3 with the following modifications: 1) liposomes were prepared with a 15:1 molar ratio of DPPC:DMPG (formula no. 3); and 2) only two doses of 240 ug of free or liposome-encapsulated tobramycin were administered to the rats.

TABLE 4

Bactericidal effect of liposomal tobramycin on *P. aeruginosa* in infected rat lung tissues

| Regimen | # rats | cfu/pair of lungs | log cfu/pair of lungs |
|---|---|---|---|
| PBS only | 3 | $1.05 \times 10^8$ | 8.02 |
| liposome-PBS (formula no. 3 without tobramycin) | 3 | $1.24 \times 10^8$ | 8.93 |
| liposome-tobra | 3 | <significant* count | <significant count |
| free tobramycin | 3 | $1.07 \times 10^6$ | 6.03 |

*None or only rare cfu (0 to 6) were visible on triplicated plates spreaded with undiluted lung samples.

The results of the experiments show that the "in situ" administration of low doses of tobramycin in lungs increases drastically the bactericidal efficacy of the encapsulated aminoglycoside comparatively to the free therapeutic agent. The very strong increase of the bactericidal efficacy of the encapsulated tobramycin indicates that the liposomal formulation allows an increased diffusion across the bacterial cell membrane and intracellular accumulation of the therapeutic agent. The drastic increase in antibacterial activity of relatively low doses of tobramycin as part of the liposomal formulation as compared to free, further suggests that the lipids of the formulations promote a fusion between the liposome and bacterial cells. The specific liposomal formulation prepared according to this invention presents original properties not shared by other earlier liposomal formulations. A case in point is the significant bactericidal activity of the tobramycin liposomal formulation on the mucoid *P. aeruginosa* strain used. Thus, the formulations of the invention appear to not only enhance the passage of the antibiotic through the OM of the bacteria but also through the exopolysaccharide thereof. Thus, the present liposomal formulations can be successfully used to treat non-mucoid and mucoid forms of bacteria. The fact that low doses of aminoglycosides are sufficient to present strong bactericidal efficacy reduces the toxicity of the antibacterial agent. In fact, the results in Tables 3 and 4 showed a drastic bactericidal activity of the antibiotic-liposomal formulation with as little as 1.37 mg of tobramycin per kg of the animal. Previously disclosed formulations used 35–120 mg/kg of antibiotic with substantially less bacterial activity (WO94/1255 and U.S. Pat. No. 4,981,692). In addition, the therapeutic liposomal formulations of the present invention are not strictly dependent on phagocytosis by macrophages as those of Popescu et al. (U.S. Pat. No. 4,981,692), designed specifically for the treatment of intracellular infections. Moreover, the fact that tobramycin concentrations observed in kidneys were lowered when encapsulated antibiotics were used comparatively to free antibiotics indicates a lowered toxicity.

In summary the present liposomal formulations provide a very significant improvement in the delivery of therapeutic agents as compared to those previously disclosed. These formulations could be used in numerous animal systems with bacterial infections. Further, the present liposomal formulation provide a promising alternative for the treatment of chronic pulmonary infections in cystic fibrosis patients.

While the invention has been described with particular reference to the illustrated embodiment, it will be understood that numerous modifications thereto will appear to those skilled in the art. Accordingly, the above description and accompanying drawings should be taken as illustrative of the invention and not in a limiting sense.

We claim:

1. A low rigidity liposomal formulation, free of cholesterol and phospholipids with high phase transition temperature ($T_C$) comprising a neutral and anionic phospholipids at a molar ratio of 5:1 to 20:1 wherein the mean value of $T_C$ is below 37° C. or below the body temperature of the animal to be treated and at least one antimicrobial agent, wherein the liposomal formulation enhances the penetration of the antimicrobial agent inside a bacterial cell by direct interaction.

2. The liposomal formulation of claim 1, wherein the neutral phospholipid and the anionic phospholipid are present at a ratio of from about 7.5 to 17.5:1.

3. The liposomal formulation of claim 1, wherein the neutral phospholipid and the anionic phospholipid are present at a ratio of about 10:1 to 15:1.

4. The liposomal formulation of claim 3, wherein the neutral phospholipid is dipalmitoylphosphatidylcholine (DPPC) and the anionic phospholipid is dimirystoylphosphatidylglycerol (DMPG).

5. The liposomal formulation of claim 1, wherein the antimicrobial agent is tobramycin at concentration from 1 ug/ml to 50 mg/ml.

6. The liposomal formulation of claim 3, wherein the antimicrobial agent is tobramycin at concentration from 1 ug/ml to 50 mg/ml.

7. The liposomal formulation of claim 4, wherein the antimicrobial agent is tobramycin at concentration from 1 ug/ml to 50 mg/ml.

8. The liposomal formulation of claim 1, wherein the formulation enhances the passage by direct interaction with bacteria of the at least one antimicrobial agent through at least one of the bacterial outer membrane and exopolysaccharide layer.

9. Method of treating a bacterial infection in mammals comprising an administration of an antimicrobial suitable dose of the liposomal formulation of claim 1 to said mammals.

10. Method of treatment of a mucoid variant of a bacterial infection in mammals comprising an administration of a suitably acceptable form of the liposomal formulation of claim 7 to said mammals.

11. Method of treatment according to claim 10, wherein the bacteria is *Pseudomonas aeruginosa, Burkholderia cepacia, Xanthomonas maltophilia, Escherichia coli*, or *Staphylococcus aureus* and the mammal is a human with cystic fibrosis or with chronic infection.

* * * * *